(12) United States Patent
Chen

(10) Patent No.: US 8,439,678 B1
(45) Date of Patent: May 14, 2013

(54) INTERPROXIMAL DENTAL STRIP

(76) Inventor: Richard S. Chen, O'Fallon, IL (US)

( * ) Notice: Subject to any disclaimer, the term of this patent is extended or adjusted under 35 U.S.C. 154(b) by 0 days.

(21) Appl. No.: 13/594,784

(22) Filed: Aug. 25, 2012

(51) Int. Cl.
*A61C 3/06* (2006.01)

(52) U.S. Cl.
USPC ........................................ 433/142

(58) Field of Classification Search ........ 433/142, 433/143, 144, 166; 132/321, 329; 451/526
See application file for complete search history.

(56) References Cited

U.S. PATENT DOCUMENTS

| | | | |
|---|---|---|---|
| 522,211 | A | 7/1894 | How |
| 1,988,065 | A * | 1/1935 | Wooddell .......................... 51/295 |
| 3,897,796 | A | 8/1975 | Erickson |
| 4,058,898 | A * | 11/1977 | Nash .............................. 433/166 |
| 4,187,082 | A * | 2/1980 | Guerra ............................ 51/295 |
| 4,450,849 | A | 5/1984 | Cerceo et al. |
| 4,563,152 | A * | 1/1986 | McClure ......................... 433/39 |
| 5,489,235 | A | 2/1996 | Gagliardi et al. |
| 5,816,808 | A | 10/1998 | Gambarini et al. |
| 5,820,450 | A | 10/1998 | Calhoun |
| 5,836,810 | A | 11/1998 | Asum |
| 6,241,522 | B1 | 6/2001 | Schon et al. |
| 6,508,649 | B2 * | 1/2003 | Gratz ............................ 433/142 |
| 6,604,534 | B2 | 8/2003 | Hill |
| 7,464,715 | B1 | 12/2008 | Husted et al. |
| 2005/0058963 | A1 | 3/2005 | Stockstill |
| 2006/0127845 | A1 | 6/2006 | Khouri |
| 2008/0038690 | A1 | 2/2008 | Allen |
| 2009/0220912 | A1 | 9/2009 | Allen |
| 2011/0200963 | A1 | 8/2011 | Allen |

* cited by examiner

*Primary Examiner* — Ralph Lewis
(74) *Attorney, Agent, or Firm* — Grace J. Fishel

(57) ABSTRACT

An interproximal dental strip with a serrated zone flanked by abrasive zones in repeated longitudinal succession along a side face of the strip. The abrasive zones have a plurality of abrasive sections with non-abrasive sections between. The abrasive sections are inclined with respect to the side edges of the strip such that only a portion of each abrasive section makes grinding contact with a tooth at any given time for more controlled and effective working of the strip.

18 Claims, 2 Drawing Sheets

INTERPROXIMAL DENTAL STRIP

BACKGROUND OF THE INVENTION

1. Field of the Invention

The present invention relates to an interproximal dental strip having a combination of a serrated zone flanked by abrasive zones, each of which has inclined spaced apart abrasive sections separated by non-abrasive sections for more controlled and effective working of the strip between the teeth.

2. Brief Description of the Prior Art

Interproximal dental strips are used in orthodontics to reduce tooth structure to correct for inadequate space caused by dental crowding or to fit bands and in restorative dentistry to trim or contour various types of restorative materials such as amalgam or resin. Typically, as a first step a strip with a serrated edge is worked between adjacent teeth until enough material is removed that an abrasive strip may be used. There are dental strips with serrations, strips with abrasives and strips with a combination of serrations and abrasives. During both the sawing and sanding operations, the strip is operated by gripping the ends and working the strip back and forth between the teeth in order to remove the undesired material. To do that, the dentist must insert at least one hand into a patient's mouth in the case of the front teeth and both hands to reach the rear teeth. In both instances, it is difficult for the dentist to control the depth of insertion of the strip between the teeth, particularly those teeth in the posterior region of the mouth, and it is not uncommon for the dental practitioner to lacerate the patient's gum or injure himself. There is also the possibility that the strip may become jammed between the teeth such that it cannot be easily worked back and forth requiring the application of additional force which increases the possibility for injury.

BRIEF SUMMARY OF THE INVENTION

In view of the above, it is an object of the present invention to provide an interproximal dental strip for more controlled and effective working of the strip between the teeth. Another object is to provide a strip which has both serrated and abrasive sections such that a dental practitioner may not need to change strips during a procedure. Other objects and features of the invention will be in part apparent and in part pointed out hereinafter.

In accordance with the invention, an interproximal dental strip to open or smooth the contact areas between teeth has two parallel side edges and two parallel side faces with at least three zones arranged in longitudinal succession along one of said parallel side faces. The middle zone is serrated along one of said parallel side edges and is flanked by abrasive zones on one of said two parallel side faces. Each abrasive zone has a plurality of spaced apart abrasive sections inclined with respect to one of the parallel side edges with a non-abrasive zone between adjacent abrasive sections. Serrations may be provided on one or both edge edges and abrasive zones may be provided on one or both side faces.

The invention summarized above comprises the constructions hereinafter described, the scope of the invention being indicated by the subjoined claims.

BRIEF DESCRIPTION OF THE SEVERAL VIEWS OF THE DRAWING

In the accompanying drawings, in which several of various possible embodiments of the invention are illustrated, corresponding reference characters refer to corresponding parts throughout the several views of the drawings in which.

DETAILED DESCRIPTION OF THE INVENTION

Figure 1:
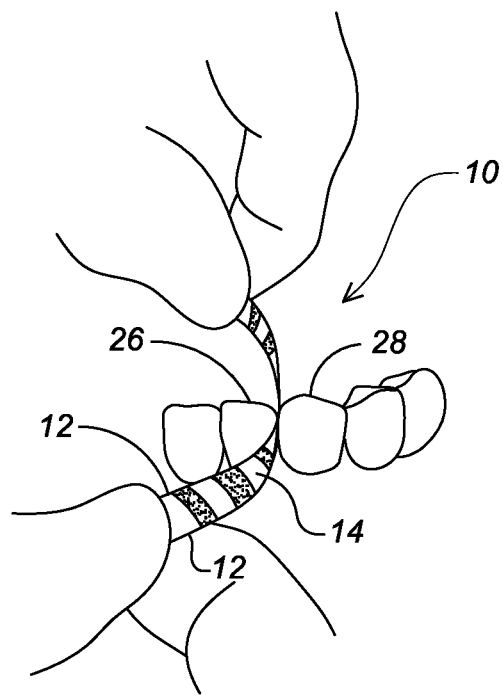
FIG. 1 is a perspective view of an interproximal strip in accordance with the present invention being worked backwards and forward between two adjacent teeth for use in removing unwanted material.
Figure 3:
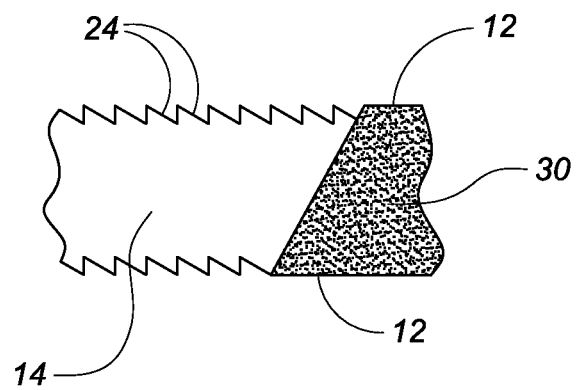
FIG. 3 is a detail on an enlarged scale taken along the line of 3-3 in FIG. 2.

Referring to the drawings more particularly by reference character, reference numeral 10 refers to an interproximal dental strip in accordance with the present invention. Dental strip 10 is a thin metal or plastic blade. Suitable materials for strip 10 must be strong and have sufficient flexibility for maneuverability within a patient's mouth. Metals for strip 10 include stainless steel, aluminum, titanium, etc. and suitable plastics include polyesters and other functionally equivalent, generally inelastic materials.

Strip 10 has two parallel side edges 12 and two parallel side faces 14. Each of the free ends of strip 10 has a gripping portion 16 for a secure gripping and handling of the dental tool. The average width of side edges 12 should be no more than about 0.2 mm, and preferably no more than about 0.05 mm to 0.1 mm to effectively fit between the teeth. Widths of about 0.05 mm allow the strip to flex during use which is helpful in accessing hard to reach areas. The average width of side faces 14 is between about 2-5 mm, for example, and the length of strip 10 may be in the order of 150 mm.

Figure 2:
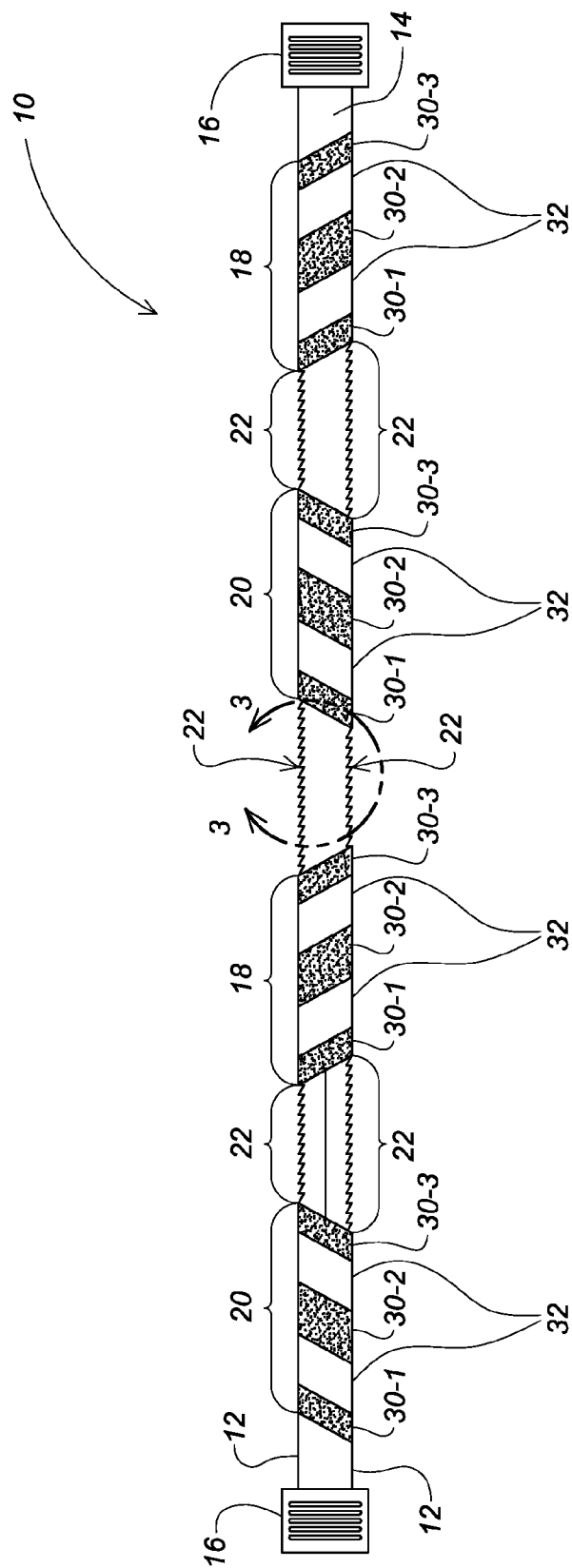
FIG. 2 is a plan view of the strip.

As best seen in FIG. 2, strip 10 has at least three zones 18, 20, 22 arranged in longitudinal succession along one of side faces 14. Middle zone 20 is serrated along at least one of side edges 12 and is flanked by abrasive zones 18, 20 on one of side faces 14. As illustrated, this pattern may be repeated along strip 10 and serrations 20 may be provided along second side edge 12 as shown. The sawteeth 24 of serrations 20 may be sloped such that strip 10 cuts in one direction as the strip is moved forward/backward between adjacent teeth 26, 28 as shown in FIG. 1. The sawteeth 24 on one side edge 12 may be coarser or finer than the sawteeth 24 on the other side edge 12.

Each of abrasive zones 18, 22 has a plurality of spaced part abrasive sections 30, three of which 30-1, 30-2 and 30-3 are shown in the drawings but the number of sections 30 are not limited to that. Each of abrasive sections 30 is a quadrilateral inclined with respect to side edges 12 with a non-abrasive section 32 provided between adjacent abrasive sections 30. The abrasive sections 30 in one abrasive zone 18 flanking serrated middle zone 20 are oppositely inclined with respect to side edges 12 to those of the other flanking abrasive zone 20.

The side edges of adjacent abrasive sections 30 may be parallel as shown, or not, and the width of the sections and the pitch distance between abrasive sections may vary. For example in a specific, but non-limiting, embodiment of the invention, the horizontal width of middle section 30-2 is 5 mm, end sections 30-1, 3-3 are 3 mm and the pitch distance forming the non-abrasive sections 32 is 5 mm. The width of the abrasive and non-abrasive sections however may be between about 2 mm and 6 mm. The angle at which abrasive sections 30 make to side edges 12 can also vary, although it cannot be nil. Preferably, however, an angle of about 45 degrees to side edges 12 is preferred.

The abrasive used for abrasive sections 30 may be of a single grit or may of different grits. The abrasive may be impregnated into, coated onto or otherwise formed on side face 14 of strip 10. Any suitable coating, such as diamond particles, with an average grain diameter in the range of approximately 8 to 150 microns may provide the abrasiveness required. Strip 10 may be single sided or double sided with respect to abrasive sections 30 and non-abrasive sections 32. Single-sided strips 10 allow for interproximal reduction on only one tooth at a time. Bilateral reduction, when appropriate, may be achieved with a double-side strip 10 without removing the strip from a patient's mouth and reversing sides.

An advantage of strip 10 is that a dentist may be able to use the same strip to reduce tooth structure without changing strips which takes time from billable practice and may lead to unacceptable patient discomfort. For example in use, serrations in middle zone 20 may be used to create a gap between adjacent teeth 26, 28. In a second step, by reciprocating abrasive sections 30 of abrasive zone 18 or 22 backwards and forwards in the gap between the teeth material is removed, either from one or both of the teeth depending on whether strip 10 is single or double-sided. The inclination of abrasive sections 30 and width of non-abrasive sections 32 provides the operator with more controlled working of the strip. Because of the inclination, only a portion of each abrasive section 30 at any given time makes grinding interface with a tooth and less force is therefore required to manipulate strip 10. With less force applied, the dental practitioner is less likely to cut into the patient's gum or injure himself. The slope of the inclined abrasive sections 30 exerts a motion on the material begin ground away perpendicular to side edges 12 thus expelling the swarf (the material being cut away). This is desirable because material lodged in abrasive sections 30 dramatically reduces the cutting action. Non-abrasive sections 30 also tend reduce loading of abrasive sections 30 by removing the swarf.

In view of the above, it will be seen that the several objects of the invention are achieved and other advantageous results attained. As various changes could be made in the above constructions without departing from the scope of the invention, it is intended that all matter contained in the above description or shown in the accompanying drawings shall be interpreted as illustrative and not in a limiting sense.

What is claimed:

1. An interproximal dental strip to open or smooth the contact areas between adjacent teeth, said strip having two parallel side edges and two parallel side faces, said strip having at least three zones arranged in longitudinal succession along one of said parallel side faces wherein a middle zone is serrated along one of said parallel side edges, said serrated zone flanked by first and second abrasive zones on one of said two parallel side faces, each abrasive zone having a plurality of spaced apart abrasive sections, each of said abrasive sections inclined with respect to one of the parallel side edges with a non-abrasive zone between adjacent abrasive sections.

2. The dental strip of claim 1 wherein the middle, first and second zones are repeated along the strip.

3. The dental strip of claim 1 wherein the middle zone is serrated along both of said parallel side edges.

4. The dental strip of claim 3 wherein the serrations in the middle zone are sawteeth sloped in one direction such that the strip cuts in one direction as the strip is moved forward and backward between the adjacent teeth.

5. The dental strip of claim 1 wherein there are three spaced apart abrasive sections in each of the first and second flanking abrasive zones.

6. The dental strip of claim 5 wherein each of the abrasive sections is a quadrilateral inclined with respect to the side edges.

7. The dental strip of claim 6 wherein the abrasive sections in the first abrasive zone are oppositely inclined with respect to the abrasive sections in the second abrasive zone.

8. An interproximal dental strip to open or smooth the contact areas between adjacent teeth, said strip having two parallel side edges and two parallel side faces, said strip having at least three zones arranged in longitudinal succession along one of said parallel side faces wherein a middle zone is serrated along one of said parallel side edges, said serrated zone flanked by first and second abrasive zones on one of said two parallel side faces, each abrasive zone having a plurality of spaced apart abrasive sections, each of said abrasive sections inclined with respect to one of the parallel side edges with a non-abrasive zone between adjacent abrasive sections, said abrasive sections in the first abrasive zone opposite inclined to the abrasive sections in the second abrasive zone.

9. The dental strip of claim 8 wherein the abrasive sections are at an angle of about 45 degrees to the side edges in the first abrasive zone.

10. The dental strip of claim 9 wherein there are three abrasive sections in each of the first and second abrasive zones.

11. The dental strip of claim 10 wherein the serrations in the middle zone are sawteeth sloped in one direction such that the strip cuts in one direction as the strip is moved forward and backward between the adjacent teeth.

12. The dental strip of claim 10 wherein a middle section of the three abrasive sections is wider than the two end abrasive sections.

13. The dental strip of claim 12 wherein abrasive sections are formed with different grits.

14. The dental strip of claim 12 wherein the horizontal width of the middle section of the three abrasive sections is about 5 mm and the two end abrasive sections are about 3 mm wide.

15. The dental strip of claim 14 wherein the horizontal width of non-abrasive zone is about 5 mm.

16. The dental strip of claim 8 wherein the middle, first and second zones are repeated along the strip.

17. The dental strip of claim 16 wherein the middle zone is serrated along both of said parallel side edges.

18. The dental strip of claim 17 wherein first and second abrasive zones are provided on both side faces.

* * * * *